(12) United States Patent
Baker et al.

(10) Patent No.: US 12,257,182 B2
(45) Date of Patent: *Mar. 25, 2025

(54) DEVICE AND METHOD OF TREATING MENOPAUSAL HOT FLASHES

(71) Applicants: Miriam Baker, Fort Lee, NJ (US); Alyssa Dweck, Armonk, NY (US); Nyiri Grigorian, Tenafly, NJ (US)

(72) Inventors: Miriam Baker, Fort Lee, NJ (US); Alyssa Dweck, Armonk, NY (US); Nyiri Grigorian, Tenafly, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/722,949

(22) Filed: Apr. 18, 2022

(65) Prior Publication Data

US 2022/0233348 A1 Jul. 28, 2022

Related U.S. Application Data

(63) Continuation of application No. 16/588,321, filed on Sep. 30, 2019, now Pat. No. 11,331,214, which is a continuation of application No. 14/913,084, filed as application No. PCT/US2015/010310 on Jan. 6, 2015, now Pat. No. 10,470,923.

(60) Provisional application No. 61/925,494, filed on Jan. 9, 2014.

(51) Int. Cl.
*A61F 7/02* (2006.01)
*A61F 7/00* (2006.01)
*A61F 7/10* (2006.01)

(52) U.S. Cl.
CPC ............... *A61F 7/02* (2013.01); *A61F 7/10* (2013.01); *A61F 2007/005* (2013.01); *A61F 2007/0219* (2013.01); *A61F 2007/0226* (2013.01); *A61F 2007/0236* (2013.01)

(58) Field of Classification Search
CPC ........ A61F 7/02; A61F 7/10; A61F 2007/005; A61F 2007/0236
See application file for complete search history.

(56) References Cited

U.S. PATENT DOCUMENTS

| 3,301,254 A | 1/1967 | Schickedanz |
| 4,382,443 A | 5/1983 | Shafer et al. |
| 4,631,062 A | 12/1986 | Lassen et al. |
| 4,688,572 A | 8/1987 | Hubbard et al. |

(Continued)

FOREIGN PATENT DOCUMENTS

| EP | 0612233 | 8/1994 |
| WO | WO 2002/47589 | 6/2002 |

OTHER PUBLICATIONS

Search Report dated Mar. 12, 2018 which issued in the corresponding European Patent Application No. 15734931.7.

(Continued)

*Primary Examiner* — Kaitlyn E Smith
(74) *Attorney, Agent, or Firm* — Crowell & Moring LLP

(57) ABSTRACT

A device and method for treatment of hot flashes in peri-menopausal and menopausal women. The device includes a cooling agent distributed over at least a portion of an area of the device, at least one liner positioned against and attached to at least one side of the cooling agent over at least the portion of the area of the device, and an adhesive. The adhesive is arranged on at least one side of the device so as to permit the device to be secured with respect to the anatomy of a user.

10 Claims, 4 Drawing Sheets

(56) References Cited

U.S. PATENT DOCUMENTS

| | | | |
|---|---|---|---|
| 4,743,245 A | 5/1988 | Lassen et al. | |
| 4,846,824 A | 7/1989 | Lassen et al. | |
| 5,167,655 A | 12/1992 | McCoy | |
| 6,068,607 A | 5/2000 | Palmer et al. | |
| 6,117,523 A | 9/2000 | Sugahara | |
| 6,461,339 B1 | 10/2002 | Sugahara | |
| 6,524,612 B2 | 2/2003 | Misumi et al. | |
| 7,291,136 B1 | 11/2007 | Drevik | |
| 8,039,011 B2 | 10/2011 | Flugge-Berendes | |
| 10,470,923 B2 * | 11/2019 | Baker | A61F 7/10 |
| 11,331,214 B2 * | 5/2022 | Baker | A61F 7/02 |
| 2002/0115976 A1 | 8/2002 | Fleming | |
| 2002/0147482 A1 | 10/2002 | Carter | |
| 2002/0193758 A1 | 12/2002 | Sandberg | |
| 2005/0070980 A1 * | 3/2005 | Noonan | A61F 7/02 |
| | | | 607/108 |
| 2005/0256497 A1 | 11/2005 | Gottwald et al. | |
| 2006/0129116 A1 | 6/2006 | Hughes | |
| 2007/0179465 A1 | 8/2007 | Sakakibara | |
| 2008/0039810 A1 | 2/2008 | Lee et al. | |
| 2008/0071336 A1 * | 3/2008 | Merriman | A61F 7/10 |
| | | | 607/113 |
| 2008/0108863 A1 | 5/2008 | Stephenson | |
| 2009/0030491 A1 * | 1/2009 | Justice-Black | A61F 7/10 |
| | | | 607/108 |
| 2009/0118574 A1 | 5/2009 | Stephenson | |
| 2009/0157153 A1 | 6/2009 | Lemke et al. | |
| 2010/0152687 A1 | 6/2010 | Carlozzi | |
| 2012/0053546 A1 * | 3/2012 | Fogg | A61F 13/84 |
| | | | 604/377 |
| 2012/0089212 A1 | 4/2012 | Benda et al. | |
| 2012/0165910 A1 * | 6/2012 | Choucair | A61F 7/10 |
| | | | 607/114 |
| 2013/0006338 A1 | 1/2013 | Emon | |
| 2013/0102983 A1 | 4/2013 | Gilmartin | |
| 2015/0119849 A1 | 4/2015 | Aronhalt et al. | |
| 2015/0282980 A1 | 10/2015 | Ogunleye et al. | |
| 2015/0320636 A1 | 11/2015 | Fine et al. | |
| 2015/0351956 A1 | 12/2015 | Enderby | |
| 2016/0022399 A1 | 1/2016 | St. Anne et al. | |
| 2017/0079836 A1 | 3/2017 | Mahon | |
| 2017/0281939 A1 | 10/2017 | St. Anne et al. | |
| 2018/0221198 A1 | 8/2018 | Mahon | |

OTHER PUBLICATIONS

Supplementary Search Report dated Jun. 28, 2017 which issued in the corresponding European Patent Application No. 15734931.7.
Communication pursuant to Article 94(3) EPC issued in counterpart European Application No. 15 734 931. 7 dated Oct. 17, 2019 (eight (8) pages).

* cited by examiner

DEVICE AND METHOD OF TREATING MENOPAUSAL HOT FLASHES

PRIORITY CLAIM

This application is a continuation of U.S. application Ser. No. 16/588,321, filed Sep. 30, 2019, which is a continuation of U.S. application Ser. No. 14/913,084, filed Feb. 19, 2016, now U.S. Pat. No. 10,470,923, issued Nov. 12, 2019, which is a U.S. national stage of application No. PCT/US2015/010310, filed Jan. 6, 2015, which claims benefit of U.S. Provisional Application No. 61/925,494, filed Jan. 9, 2014, the disclosures of which are expressly incorporated by reference herein.

FIELD OF THE INVENTION

The present invention is directed to a device and method for treating menopausal hot flashes. The device comprises a thin cushion or pad having an outer surface surrounding a cooling substance such as a gel. The device is designed to wear inside the underwear against and in contact with the clitoris to provide a cooling sensation to the sensitive nerve endings of the clitoris on a continual basis. In the method, the device is applied to the clitoris in such a way as to cause the sensitive nerve endings bundled in the clitoris to disseminate the sense of cooling throughout the body to treat the effects of hot flashes experienced by the wearer of the device. The device works with the clitoris and/or the brain to give the perception of cooling. The cooling effect may be real or perceived, giving the wearer a sense of control over vasomotor symptoms.

BACKGROUND OF THE INVENTION

The median age for the onset of menopause in the United States is 51. 50-80% of peri-menopausal women (i.e., women transitioning to menopause) and menopausal women experience hot flashes and night sweats.

A hot flash, sometimes called a hot flush, is a quick feeling of heat, sometimes accompanied by a red flushed face and sweating. The exact cause of hot flashes is not known, but it may be related to changes in thermoregulation and/or blood circulation. In particular, hot flashes can occur when the blood vessels nears the skin's surface dilate to cool. A woman may also sweat at such time in an attempt to cool the body. In some women this is accompanied by an increased heart rate or chills. Hot flashes that occur at night are called night sweats and can adversely affect sleep. Moreover, stress, caffeine, alcohol, spicy foods, heat, cigarette smoke and tight clothing, among other things, are believed to trigger hot flashes. Importantly, hot flashes can occur randomly and unexpectedly, thus leading the sufferer to experience anxiety as a result of the uncertainty of if/when such event may occur.

Current treatments commonly prescribed for hot flashes include Hormone Replacement Therapy (HRT), low-dose anti-depressants, including Selective Serotonin Reuptake Inhibitors (SSRIs), Clonidine, a blood pressure medication, Gabapentin, an anti-seizure drug, Brisdelle®, a paroxetine formula specifically for hot flashes, and Duavee®, a conjugated estrogen/bazedoxifene formal designed to treat hot flashes. However, the use of such drugs, such as SSRIs, can be associated with side effects. In addition, some women cannot or prefer not to take medication. Other homeopathic remedies, such as soy products, phytoestrogens and evening primrose oil, have also been suggested. However, their effectiveness is unproven and anecdotal at best.

Thus, there exists a need for an alternative product and treatment method to alleviate the adverse effects of hot flashes that do not present the drawbacks of the methods discussed above.

SUMMARY OF THE INVENTION

In accordance with a first aspect of the present invention, a device is disclosed for treatment of hot flashes in peri-menopausal and menopausal women. The device has a cooling agent distributed over at least a portion of an area of the device, at least one liner positioned against and attached to at least one side of the cooling agent over at least the portion of the area of the device, and an adhesive. The adhesive is arranged on at least one side of the device so as to permit the device to be positionally affixed with respect to the anatomy of a user. The device is shaped so that, when positioned for wear using the adhesive, at least a portion of the device having the cooling agent is positioned proximate the clitoris, its crurae and/or vulva, of the user and, to the extent any portion of the device is proximate the urethra of the user, the urethra-proximate portion is devoid of the cooling agent.

In one embodiment, the device is intended to be received in an undergarment having a pocket so that adhesive on the device is not needed but, rather, the position of the pocket maintains the device in a proper position with respect to the anatomy of the user.

In another embodiment, the device is configured as a heart-shaped pad having a tip portion and two rounded bottom portions, and wherein the cooling agent is distributed in the pad at least at the tip portion, and preferably, also at the two rounded bottom portions.

In yet another embodiment, the device includes upper and lower liners, with the upper and lower liners sandwiching the cooling agent over at least a portion of the area of the device.

Still other embodiments are disclosed with reference to the following drawings, description and claims.

BRIEF DESCRIPTION OF THE DRAWINGS

The above and/or other aspects and advantages will become more apparent and more readily appreciated from the following detailed description of the disclosed embodiments taken in conjunction with the accompanying drawings in which.

DETAILED DESCRIPTION OF THE PRESENTLY PREFERRED EMBODIMENTS

Figure 1:
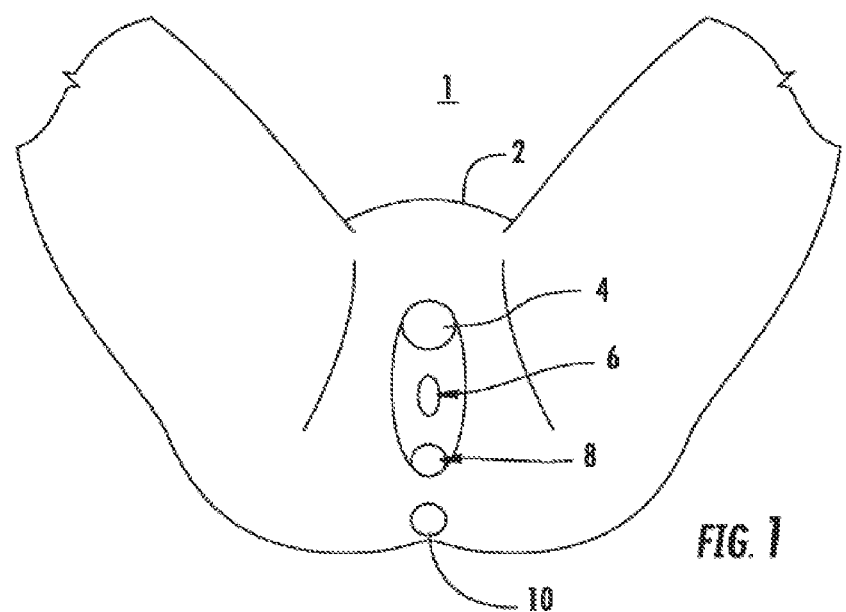
FIG. 1 is a diagram of a portion of the female anatomy affected by the device and method of the present invention.

In the following description, like elements will be referred to using like reference numerals.

An exact cause of menopausal hot flashes is not known. What is known is that a slight increase in body core temperature, stress and a multitude of external variables can be primary triggers. It has been discovered that keeping the baseline body temperature lower consistently produces relief or may aide in prevention of the hot flash. Doing so in a discrete manner so as to not draw attention to the person experiencing the hot flash, while also presenting a discrete and comfortable treatment device and method is of importance.

The clitoris has an extremely rich blood and nerve supply and includes erectile tissue which allows for a very small surface area to be influenced by the application of a cooling sensation. The inventors have discovered that application of a cooling sensation to the clitoris, the crurae, and preferably to the labia as well, alleviates vasomotor symptoms associated with hot flashes. The clitoris is unique and distinct from other skin surfaces to provide this effect. In view of this, a device configured as a cooling pad in accordance with the present invention has the effect, be it real or perceived, of lowering or keeping consistent, existing body temperature, thereby ameliorating hot flashes.

Taking advantage of the particular characteristic of the clitoris, in the disclosed embodiments of the present invention, a cooling device, preferably configured as a pad having an enclosed cooling agent, such as a gel, is applied proximate or directly against the clitoris, and preferably proximate or directly against the labia as well.

As used herein, the term "proximate" means a location sufficiently close such that when the pad is in its intended position, the clitoris (and, optionally the labia as well) will experience cooling sensation from the cooling device. Thus, the pad may be directly in contact with the wearer, have a layer of material disposed between the pad and the wearer, or otherwise be sufficiently close to the wearer, so long as the therapeutic cooling effect is realized by the wearer. As described below, the cooling agent is applied by the pad, which is positioned in a way so as to be proximate to, or directly contact, the clitoris. The pad is preferably shaped so as to apply the cooling sensation of the cooling agent to the clitoris and labia, but preferably not to the urethra or vaginal opening.

Figure 2:
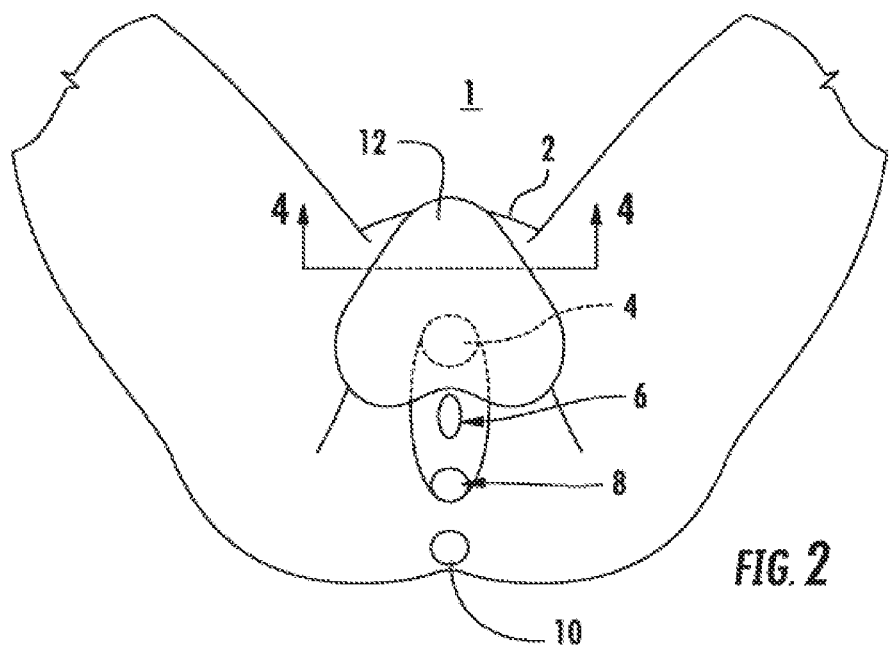
FIG. 2 is a diagram showing the positioning of a device in use in relation to the portion of the female anatomy shown in FIG. 1.

FIG. 1 is a schematic view showing a groin area 1 of a woman in which is located the mons pubis 2, clitoris 4, urethra 6, the vaginal entrance 8 and anus 10. FIG. 2 shows a cooling device 12 configured as a pad 12 according to an embodiment of the present invention, applied, in use, so as to contact or be proximate to the clitoris 4. As will be described in greater detail below, the pad 12 is configured so as to be filled with a cooling agent, a salt or gel, such that the positioning of the pad 12 respect to the clitoris 4, in particular, provides a cooling sensation and, hence, relief from hot flashes.

A preferred gel for the cooling agent is the gel used in the headache relief treatment, Be Koool®, by Kobayashi Health Care, which comprise water, a polymer, menthol and a preservative. This gel provides cooling by an evaporation process which can remain effective for 6-8 hours.

Preferably, the pad 12 is usable, and then disposable after use. In a preferred embodiment, the pad 12 is "heart-shaped", as shown in FIG. 3, with approximately 2-6 inches of circumference, and as thin as possible for purposes of comfort to the wearer, with a longest dimension of approximately 3 inches.

Figure 3:
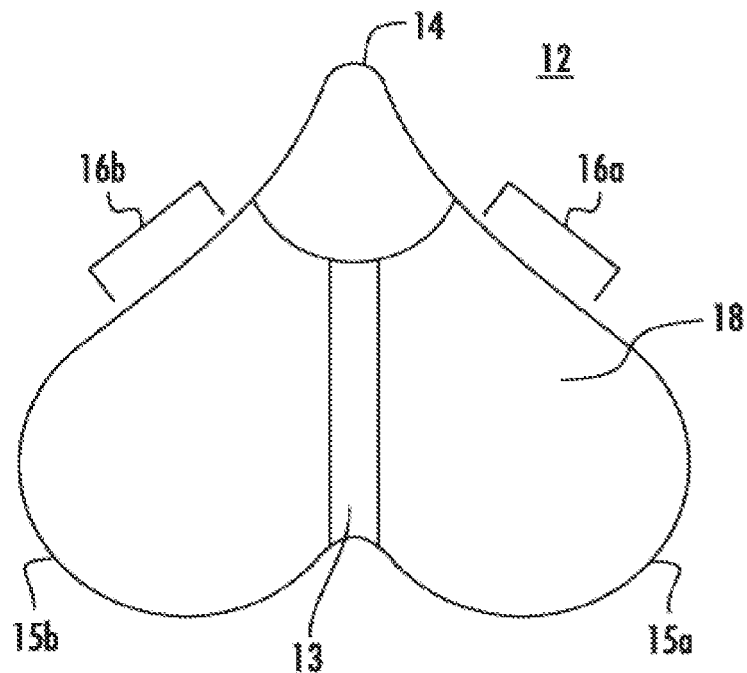
FIG. 3 is a view of the device in accordance with an embodiment of the present invention.

As shown in FIG. 3, the pad 12 has an adhesive area 13 on a side away from the wearer, for attachment to the inside of an undergarment, such as panties. The pad 12 is preferably designed such that a tip 14 of the heart shaped configuration of the pad 12 rests at the top of the clitoris 4 with rounded heart sections 15a and 15b of the pad 12 resting along the top of the labia of the vulva (not shown). In this embodiment, the tip 14 and the rounded heart sections 15a and 15b are filled with the cooling agent 18. As discussed above, this cooling agent 18 is preferably of gel, of the type discussed above, and/or other material that can maintain a cooling sensation to the areas to which it is applied to a degree, and for a sufficient duration to provide the wearer with relief of hot flashes.

The cooling material used will preferably be one that will maintain a temperature of the cooling material and/or of the anatomy portion in proximity of contact with the cooling material in a range of about 34 degrees to 50 degrees and duration long enough to remain effective in providing cooling therapy to the wearer. The action of preferred cooling agents may also be of the type released primarily by manipulating: shaking, pressing or folding, or applying any other force prior to use, such as those provided in cooling packs often found in first aid kids. However the invention is not limited to the types of cooling agents discussed above and may instead maintain it cooling properties by having been previously placed in a low temperature environment, such as, for example, a cooler, refrigerator, or other cooling apparatus.

In the embodiment shown in FIG. 3, the pad 12 in addition to, or instead of, the adhesive portion 13, has wings 16a and 16b, each with an adhesive, to adhere the pad to the wearer's undergarment and maintain the pad in proper position for the desired therapeutic effect. These wings are provided with adhesive which permits the pad to be secured in position, or further secured when used in conjunction with adhesive 13, for example, by attaching the wings 16a and 16b to the inner area of panties worn by the user. The adhesive used for the present invention is preferably one that will adhere securely, but removably, to an undergarment.

Figure 4:
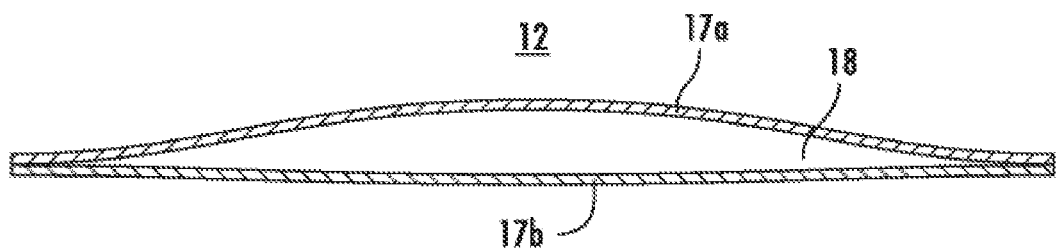
FIG. 4 is a cross-section view of the device at line 4-4' in FIG. 2.

FIG. 4 is a sectional view taken at lines 4-4' in FIG. 2. As can be seen in this figure, the pad 12 has a multi-layer arrangement, with the cooling agent 18 sandwiched between upper and lower layers 17a and 17b of a soft material, such as cotton and/or other fabric. The soft fabric material of the lower layer 17b provides comfort and provides at least some degree of separation between the actual cooling agent and the wearer. This may be particularly important because the part of the body to which the pad is applied is comprised of sensitive skin which may also be hair-bearing. The casing/material of the pad is preferably one that is pervious to sweat, such as for example, on the side of the pad that contacts the wearer, cotton (lower layer 17b), while the upper layer should be made of a material that provides for moisture wicking, to allow evaporation to occur, for example to allow moisture and vapor to escape from the side of the pad away from the user's body (upper layer 17a). An example of such a wicking fabric is undyed cotton.

By virtue of the disclosed shape of the pad 12, the pad 12 preferably is contoured with respect to the female anatomy so as to only apply the cooling sensation to desired areas, in this case the clitoris 4 and labia, while avoiding the application of cooling sensation to other areas, most notably, the urethra 6 or opening to the vagina 8. Avoiding the area of the urethra is particularly preferred as contact with the pad 12, or at least the cooling agent, to the urethra 6 may create discomfort or urgency to urinate. While the pad may, in some embodiments, have portions that contact, for example, the urethra, it is preferable if the cooling agent is provided only in portions of the pad 12, such as the tip 14 and the lower portions 15a and 15b that would be positioned over the clitoris and labia during wear.

In particular, the cooling agent 18 may be distributed throughout the area of the pad 12, in which case the pad itself is configured to avoid applying a cooling sensation to the urethra. Alternatively, the pad may be configured to contact the urethra, in which case, that portion of the pad in contact with the urethra will be devoid of cooling agent.

Figure 5:
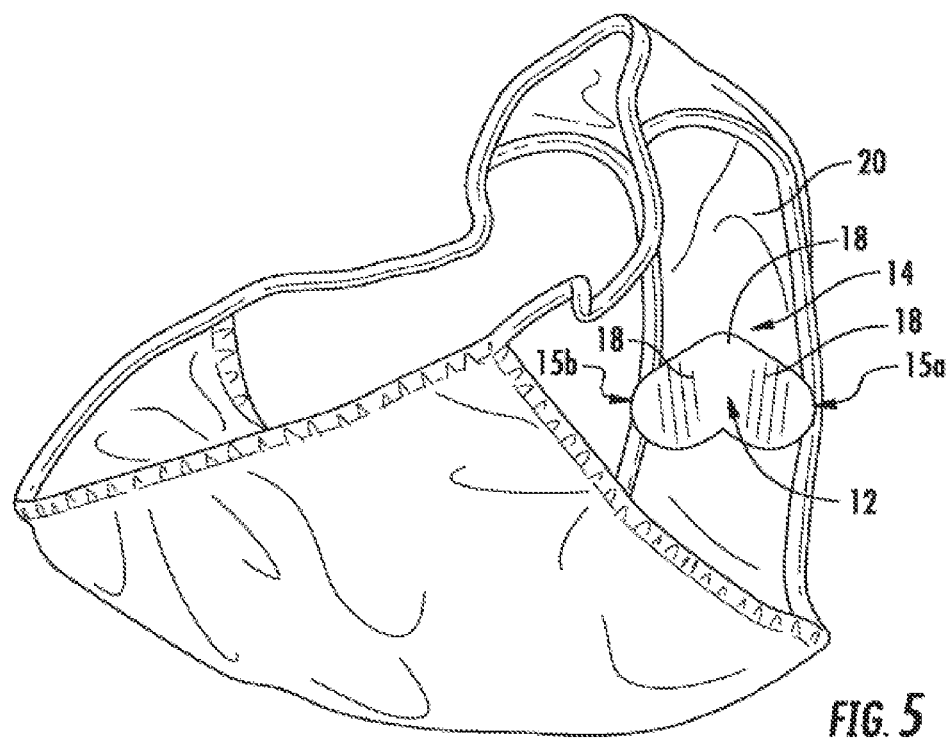
FIG. 5 is a view showing the device positioned on an undergarment according to one embodiment of the present invention.

In one embodiment, the device has an adhesive backing covered by a removable mask. The mask can be peeled back to expose the adhesive so that the device can be releasably adhered to the inside of an undergarment. An example of such an embodiment is shown in FIG. 5, in which the pad 12 is affixed, for example by an adhesive located along an edge of the pad 12 away from view, the adhesive touching the fabric of the panties 20 and securing the pad 12 in position. The cooling agent 18 may be distributed primarily at the region of the tip 14 and at the region of the rounded heart sections 15a and 15b, and enclosed within the layers 17a and 17b. Alternatively, the cooling agent may be distributed throughout the pad 12, in which case the pad 12 is dimension such that it does not contact the urethra of the user.

Figure 6:
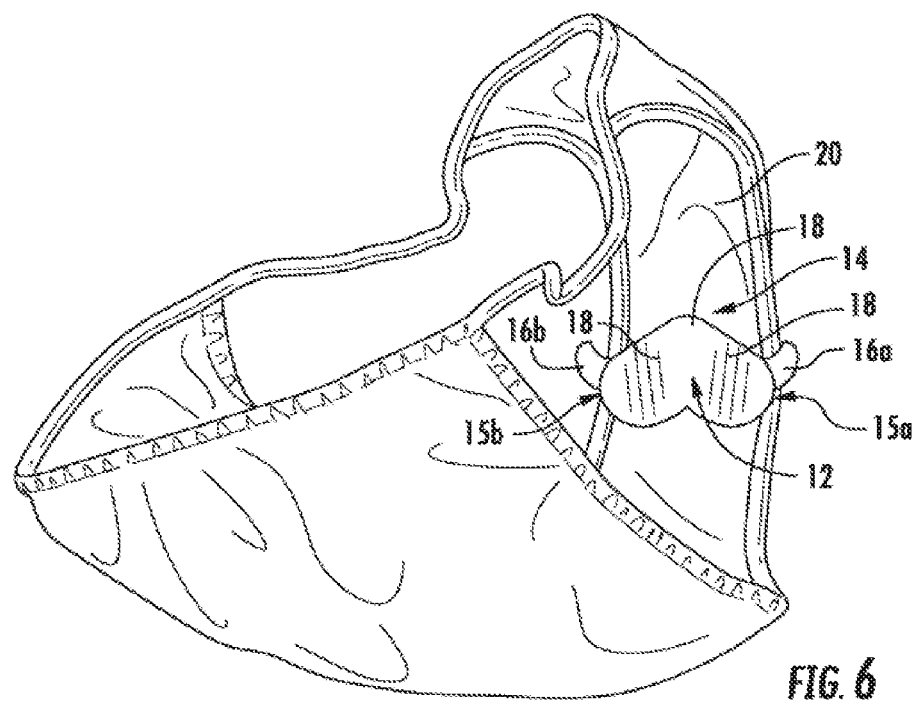
FIG. 6 is another view showing the device positioned on an undergarment.

FIG. 6 shows a variation on the pad 12 of the present invention in which the wings 16a and 16b are used, instead of, or in addition to other adhesive areas, to affix the pad 12 to the inside of panties. The wings 16a and 16b have a removable backing material, not visible in the figure, which, once removed, expose the sticky adhesive surface. The wings thus affixed to, e.g., panties, maintain the proper position of the pad 12 in relation to the portions of the woman's anatomy to be cooled.

Figure 7:
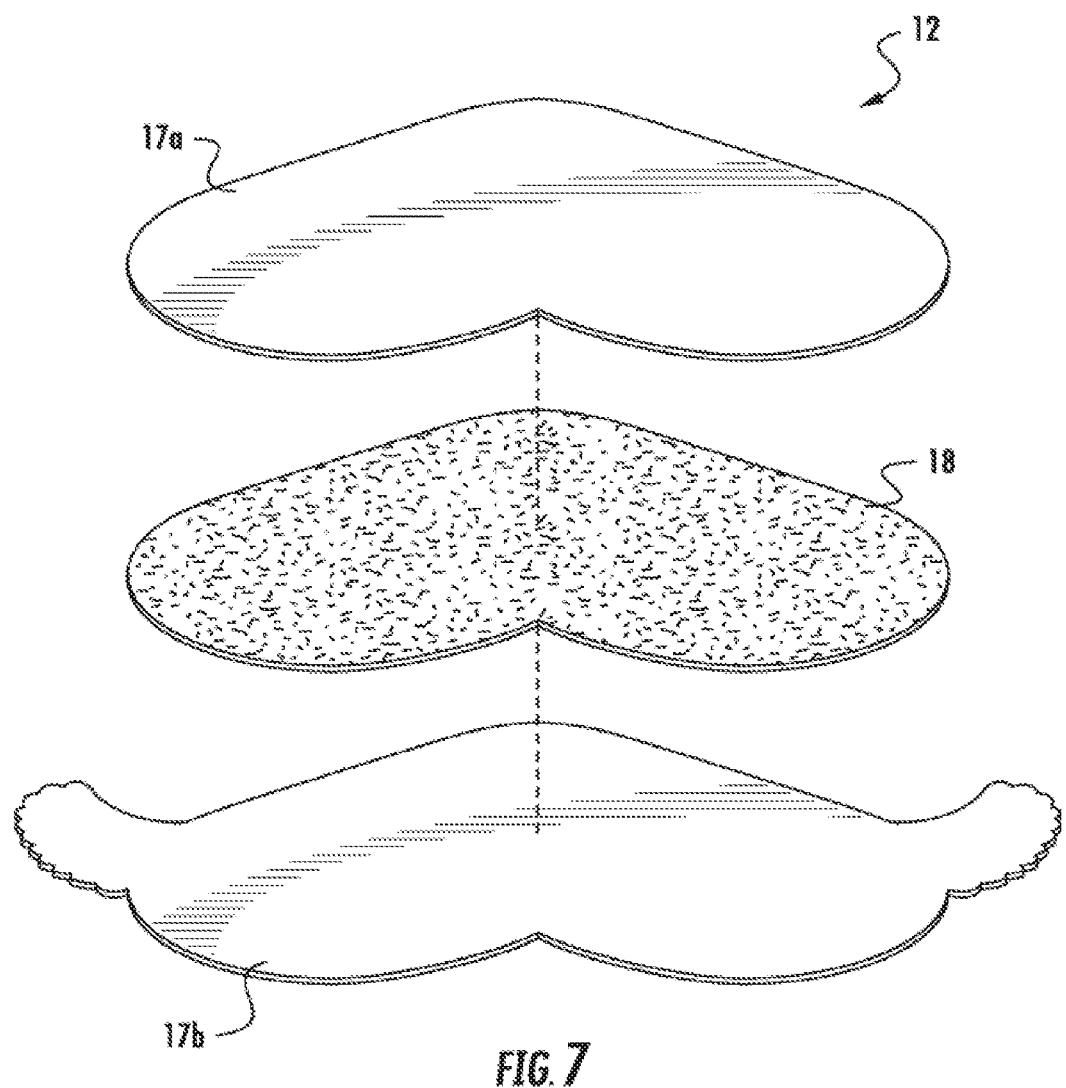
FIG. 7 is an exploded view of the device according to an embodiment of the present invention.

FIG. 7 is an exploded view of the pad 12. As can been in the figure, the fabric upper and lower layers 17a and 17b are provided above and below the cooling agent 18 which, in the exploded view, is shown as a textured gel package. In this case, layer 17a has the wings and would be, in use, furthest from the wearer's body. The layers 17a, 17b, and cooling agent 18, are preferably subsequently fused together, for example by a lamination process to produce the finished pad 12.

In accordance with another embodiment, not shown, the device can be integrated into a garment or undergarment, such as underwear, pantyhose, leggings, tights, and the like. For example, a panty may be provided that has a pocket in which the pad 12 can be inserted. In such case, the pad will not be directly in contact with the wearer but will be in sufficient proximity to the wearer such that the cooling effect of the cooling agent will be effective as applied to the clitoris (and optionally also the labia).

In accordance with another aspect of the invention, a method of treating menopausal hot flashes is provided. In the method, the pad 12, as described above, is provided proximate the clitoris of a woman experiencing, or concerned about experiencing, hot flashes, such that the tip 14 is proximate the clitoris and the lower heart shaped sections 15a and 15b of the pad are positioned proximate the labia, for a period of time sufficient to reduce or eliminate hot flashes while the device is in use. The method also preferably includes removing the old pad and applying a new pad once the cooling effect of the old pad has become reduced. The efficacy of the cooling effect can be short term and repeated with each new pad application due to the richness of nerve and blood supply in the clitoris.

The pad 12 according to the present invention can be used, in accordance with the method of the present invention, at bedtime for sleep comfort when hot flashes can often become troublesome, or during the day, and can be prophylactic in that its use can be anticipated; e.g., usage can be tailored to a hot day, physical activity and/or stress level of the wearer.

By virtue of the pad 12 and the associated method, relief from hot flashes can be provided based on a product that is available over-the-counter, is easy to use, and is disposable and discreet. Moreover, unlike certain prior art treatments, it is appropriate for women with breast and other hormone sensitive cancers, and is safe to use together with other medications.

Advantageously, the pad 12 can be used at bedtime to provide sleep comfort when hot flashes and night sweats cause significant sleep disruption. Also, the pad 12 is disposable and provides a cooling effect lasting 6-8 hours, with a residual cooling effect upon removal.

By virtue of the structure of the pad 12, it is portable in the form of a disposable feminine hygiene product, namely, a disposable pad, which allows the device to be easily carried or stored in one's pocket/bag/desk/briefcase, etc., and can be used when needed. Thus, anxiety that is oftentimes associated with sufferers of hot flashes—which anxiety may stem from the randomness of when hot flashes may/will occur—can be ameliorated by providing a ready-to-use treatment method in the form of the disclosed pad 12.

Another advantageous effect of the pad 12 and method of the present invention is the ability to put into place a direct cooling system that is efficient in its immediate effect on cooling the body, and offers amelioration/prevention of hot flash symptoms.

Thus, while there have been shown and described and pointed out fundamental novel features of the invention as applied to a preferred embodiment thereof, it will be understood that various omissions and substitutions and changes in the form and details of the devices illustrated, and in their operation, maybe made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A device used for providing relief from hot flashes in perimenopausal and menopausal women, the device consisting of:
    a cooling agent distributed over at least a portion of an area of the device, wherein the cooling agent is a gel utilizing polymer;
    the device is configured as a heart-shaped pad having a tip portion and two rounded bottom portions, and wherein the cooling agent is distributed in the pad at least at the tip portion and at the two rounded bottom portions, wherein the tip portion is positioned over the clitoris of the user and the two rounded bottom portions are positioned over the labia of the user;

at least one liner positioned against and attached to at least one side of the cooling agent over at least the portion of the area of the device, wherein the at least one liner comprises upper and lower liners; and an adhesive, the adhesive being arranged on at least one side of the device so as to permit the device to be positionally affixed with respect to the anatomy of a user, wherein the portion of the device having the cooling agent, when positioned for wear, is in direct contact with the clitoris and labia of the user to provide a cooling sensation to the clitoris and the labia and is not in direct contact with the urethra, vagina, and/or anus of the user.

2. The device of claim 1, wherein the upper and lower liners sandwiching the cooling agent over at least the portion of the area of the device.

3. The device of claim 2, wherein the adhesive has a removable adhesive backing.

4. The device of claim 2, wherein the adhesive is configured to affix the device to a garment such that cooling agent remains properly positioned in an intended manner when the garment is worn.

5. The device of claim 1, wherein the adhesive has a removable adhesive backing.

6. The device of claim 1, wherein the adhesive is configured to affix the device to a garment such that cooling agent remains properly positioned in an intended manner when the garment is worn.

7. The device of claim 1, wherein when the device is positioned for wear, the lower liner contacts the user's body and the upper liner is positioned on an opposite side of the device.

8. The device of claim 7, wherein the lower liner comprises a material that is pervious to sweat.

9. The device according to claim 7, wherein the upper liner comprises a material that provides moisture wicking.

10. A device for use with an undergarment for providing relief from hot flashes in perimenopausal and menopausal women, the device consisting of:

a cooling agent distributed over at least a portion of an area of the device, wherein the cooling agent is a gel utilizing polymer;

the device is configured as a heart-shaped pad having a tip portion and two rounded bottom portions, wherein the cooling agent is distributed in the pad at least at the tip portion and at the two rounded bottom portions, wherein the tip portion is positioned over the clitoris of the user and the two rounded bottom portions are positioned over the labia of the user;

the device has at least one liner positioned against and attached to at least one side of the cooling agent over at least the portion of the area of the device, wherein the at least one liner comprises an upper and lower liners sandwiching the cooling agent; and an adhesive, the adhesive being arranged on at least one side of the device so as to permit the device to be positionally affixed with respect to the anatomy of a user, wherein the portion of the device having the cooling agent is in direct contact with the clitoris and labia of the user to provide a cooling sensation to the clitoris and the labia and is not in direct contact with the urethra, vagina, and/or anus of the user.

* * * * *